US012251166B2

United States Patent
Vaidya et al.

(10) Patent No.: US 12,251,166 B2
(45) Date of Patent: Mar. 18, 2025

(54) SYSTEM AND METHOD FOR ESTIMATING LOCATION OF TIP OF INTERVENTION DEVICE IN ACOUSTIC IMAGING

(71) Applicant: KONINKLIJKE PHILIPS N.V., Eindhoven (NL)

(72) Inventors: Kunal Vaidya, Boston, MA (US); Ameet Kumar Jain, Boston, MA (US); Hendrik Roelof Stapert, Eindhoven (NL); Ramon Quido Erkamp, Swampscott, MA (US); Shyam Bharat, Arlington, MA (US); Alvin Chen, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 973 days.

(21) Appl. No.: 17/286,859

(22) PCT Filed: Oct. 22, 2019

(86) PCT No.: PCT/EP2019/078644
§ 371 (c)(1),
(2) Date: Apr. 20, 2021

(87) PCT Pub. No.: WO2020/083863
PCT Pub. Date: Apr. 30, 2020

(65) Prior Publication Data
US 2021/0378758 A1 Dec. 9, 2021

Related U.S. Application Data

(60) Provisional application No. 62/750,495, filed on Oct. 25, 2018.

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/14* (2013.01); *A61B 8/463* (2013.01);
(Continued)

(58) Field of Classification Search
CPC ......... A61B 34/20; A61B 8/0841; A61B 8/14; A61B 8/463; A61B 2034/2063;
(Continued)

(56) References Cited

U.S. PATENT DOCUMENTS

| 4,249,539 | A | 2/1981 | Vilkomerson |
| 2007/0073155 | A1* | 3/2007 | Park ..................... A61B 8/0833 600/461 |

(Continued)

FOREIGN PATENT DOCUMENTS

| JP | 2015198888 A | 11/2015 |
| WO | 2013108198 A1 | 7/2013 |

(Continued)

OTHER PUBLICATIONS

International Search Report and Written Opinion of PCT/EP2019/078644, dated Feb. 4, 2020.

*Primary Examiner* — Bo Joseph Peng

(57) ABSTRACT

An acoustic imaging apparatus and method receive a sensor signal from a passive sensor disposed on a surface of an intervention device which is disposed in an area of interest, wherein the passive sensor is located at a fixed distance from the tip of the intervention device. A processor is configured to ascertain an estimated range of locations of the tip of the intervention device in an image plane by using the sensor signal and an estimated effective distance, projected onto the image plane, from the passive sensor to the tip of the intervention device.

21 Claims, 9 Drawing Sheets

(51) Int. Cl.
- *A61B 8/08* (2006.01)
- *A61B 8/14* (2006.01)
- *G06T 7/11* (2017.01)
- *G06T 7/149* (2017.01)
- *G06T 7/73* (2017.01)

(52) U.S. Cl.
CPC ................ *G06T 7/11* (2017.01); *G06T 7/149* (2017.01); *G06T 7/74* (2017.01); *G06T 7/75* (2017.01); *A61B 2034/2063* (2016.02); *G06T 2207/10132* (2013.01); *G06T 2207/30004* (2013.01); *G06T 2207/30241* (2013.01)

(58) Field of Classification Search
CPC .......... A61B 8/461; G06T 7/11; G06T 7/149; G06T 7/74; G06T 7/75; G06T 2207/10132; G06T 2207/30004; G06T 2207/30241
See application file for complete search history.

(56) References Cited

U.S. PATENT DOCUMENTS

| | | | |
|---|---|---|---|
| 2010/0076305 A1* | 3/2010 | Maier-Hein | A61B 6/12 600/426 |
| 2011/0201931 A1* | 8/2011 | Palmeri | G06T 7/0016 600/440 |
| 2014/0276003 A1 | 9/2014 | Wang | |
| 2014/0323854 A1 | 10/2014 | Takeda | |
| 2015/0297114 A1 | 10/2015 | Cox | |
| 2018/0000446 A1 | 1/2018 | Lu | |

FOREIGN PATENT DOCUMENTS

| | | | | |
|---|---|---|---|---|
| WO | 2016103094 A1 | | 6/2016 | |
| WO | 2017102369 A1 | | 6/2017 | |
| WO | WO2017/102369 | * | 6/2017 | ............ G01S 15/89 |
| WO | 2017192603 A1 | | 11/2017 | |

* cited by examiner

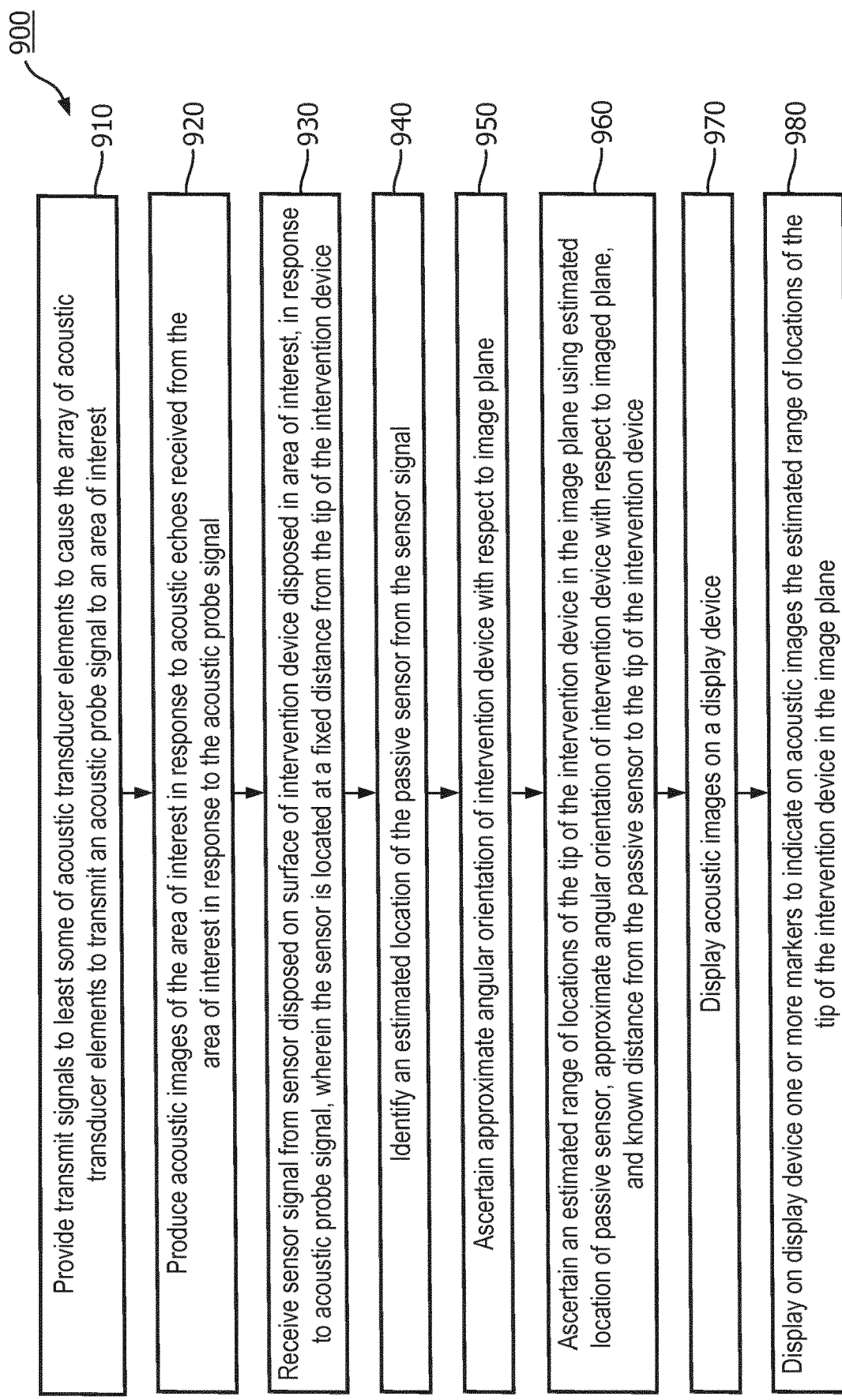

SYSTEM AND METHOD FOR ESTIMATING LOCATION OF TIP OF INTERVENTION DEVICE IN ACOUSTIC IMAGING

CROSS-REFERENCE TO PRIOR APPLICATIONS

This application is the U.S. National Phase application under 35 U.S.C. § 371 of International Application No. PCT/EP2019/078644, filed on Oct. 22, 2019, which claims the benefit of U.S. Provisional Patent Application Ser. No. 62/750,495, filed Oct. 25, 2018. These applications are hereby incorporated by reference herein.

TECHNICAL FIELD OF THE INVENTION

This invention pertains to acoustic (e.g., ultrasound) imaging, and in particular a system, device and method for estimating the location of the tip of an instrument in acoustic images employed in conjunction with an interventional procedure.

BACKGROUND AND SUMMARY OF THE INVENTION

Acoustic (e.g., ultrasound) imaging systems are increasingly being employed in a variety of applications and contexts. For example, ultrasound imaging is being increasingly employed in the context of ultrasound-guided medical procedures.

Intervention devices such as catheters and needles are known which have a sensor disposed on a surface thereof at a location near the tip for identification of the intervention instrument in acoustic images produced by an acoustic imaging system. For example, U.S. Pat. No. 4,249,539 describes an arrangement in which a medical needle includes an ultrasound transducer which is responsive to the ultrasound signals emitted by an ultrasound imaging system. Upon detecting an ultrasound pulse from the ultrasound imaging system, a circuit connected to the transducer triggers the insertion of an indication of the transducer position into the ultrasound image through either the generation of a return ultrasound pulse from the transducer, or through the simulation of such a return pulse using a time of flight delay.

In order to successfully perform an interventional procedure using one or more needles, the tip(s) of the needle(s) is/are the focus of attention. Accordingly, in ultrasound-guided medical procedures the physician wants to be able to visually locate the current position of the needle tip (or catheter tip) in acoustic images which are displayed on a display screen or monitor. In order to ensure safety, the displayed needle tip position must never lag the actual tip position.

However, for many intervention devices such as needles, it is not possible or practical to place a sensor or tracking device right at the tip of the device. The mechanical constraints of such instruments limit the ability to position the sensor at-will, for example at the tip of a needle where it might interfere with insertion.

Due to the inability to place the sensor on the tip of an intervention device such as a needle, the location of the sensor on the needle shaft is offset from the tip by a distance, D, which may vary from need to device. For some typical instruments, the distance D may be about 1.5-2 mm. The position of the sensor may be visually communicated to the end user by plotting a circle on the ultrasound image such that the tip lies on or inside the displayed circle. Clinicians typically use their judgment to determine the location of the tip within the circle. The ability to reduce this region of uncertainty is very beneficial in ensuring safe execution of interventional procedures.

Using two or more sensors, as disclosed by U.S. Patent Application Publication 2018/00044 may solve this problem, but this adds to the cost of the intervention device and the acoustic imaging system, which can be crucial in low margin procedures.

Accordingly, it would be desirable to provide a system and a method which can provide more accurate estimates of the location of a tip of an intervention device such as a surgical needle, in acoustic images. In particular it would be desirable to provide such a system and method which can operate with a single sensor disposed on a surface of the intervention device.

In one aspect of the invention, a system comprises: an acoustic probe having an array of acoustic transducer elements; and an acoustic imaging instrument connected to the acoustic probe and configured to provide transmit signals to least some of the acoustic transducer elements to cause the array of acoustic transducer elements to transmit an acoustic probe signal to an area of interest, and further configured to produce acoustic images of an image plane of the area of interest in response to acoustic echoes received from the area of interest in response to the acoustic probe signal. The acoustic imaging instrument includes: a display device configured to display the acoustic images of the image plane in the area of interest; a receiver interface configured to receive a sensor signal from a passive sensor disposed on a surface of an intervention device disposed in the area of interest, the sensor signal being produced in response to the acoustic probe signal, wherein the passive sensor is located at a fixed distance from the tip of the intervention device; and a processor. The processor is configured to: identify an estimated location of the passive sensor from the sensor signal, ascertain an approximate angular orientation of the intervention device with respect to the image plane, and ascertain an estimated range of locations of the tip of the intervention device in the image plane using the estimated location of the passive sensor, the approximate angular orientation of the intervention device with respect to the image plane, and the known distance from the passive sensor to the tip of the intervention device. The display device is further configured to display one or more markers to indicate on the acoustic images the estimated range of locations of the tip of the intervention device in the image plane.

In some embodiments, the one or more markers includes a circle having a first color for a majority of its circumference and having a second color for an arc of less than 90 degrees, wherein the second color indicates most likely locations of the tip of the intervention device.

In some embodiments, the intervention device is a surgical needle.

In some embodiments, the processor is configured to ascertain the estimated range of locations of the tip of the intervention device in the image plane by ascertaining an effective in-plane tip-to-sensor distance between the passive sensor and the tip of the intervention device in the image plane based on the approximate angular orientation of the intervention device with respect to the image plane, and the fixed distance from the passive sensor to the tip of the intervention device.

In some embodiments, the processor is configured to ascertain the approximate angular orientation of the intervention device with respect to the image plane by using a history of previous positions of the intervention device and prediction of a future path of the intervention device by employing a Kalman model.

In some embodiments, the processor is configured to ascertain the approximate angular orientation of the intervention device with respect to the image plane by monitoring an insertion point of the intervention device within a patient to estimate a trajectory of the needle.

In some embodiments, the processor is configured to ascertain the approximate angular orientation of the intervention device with respect to the image plane by segmenting a shaft of the intervention device in the acoustic images.

In some embodiments, the processor is configured to ascertain the approximate angular orientation of the intervention device with respect to the image plane by finding a best fit match to: a history of previous positions of the intervention device and prediction of a future path of the intervention device by employing a Kalman model; a monitored insertion point of the intervention device within a patient; and a segmented shaft of the intervention device in the acoustic images.

In another aspect of the invention, a method comprising: transmitting an acoustic probe signal to an area of interest; producing acoustic images of an image plane of the area of interest in response to acoustic echoes received from the area of interest in response to the acoustic probe signal; receiving a sensor signal from a passive sensor disposed on a surface of an intervention device in the area of interest, the sensor signal being produced in response to the acoustic probe signal, wherein the passive sensor is located at a fixed distance from the tip of the intervention device; identifying an estimated location of the passive sensor from the sensor signal; ascertaining an approximate angular orientation of the intervention device with respect to the image plane; ascertaining an estimated range of locations of the tip of the intervention device in the image plane using the estimated location of the passive sensor, the approximate angular orientation of the intervention device with respect to the image plane, and the known distance from the passive sensor to the tip of the intervention device; displaying the acoustic images on a display device; and displaying on the display device one or more markers to indicate on the acoustic images the estimated range of locations of the tip of the intervention device in the image plane.

In some embodiments, the one or more markers includes a circle having a first color for a majority of its circumference and having a second color for an arc of less than 90 degrees, wherein the second color indicates most likely locations of the tip of the intervention device.

In some embodiments, the intervention device is a surgical needle.

In some embodiments, ascertaining the estimated range of locations of the tip of the intervention device in the image plane comprises ascertaining an effective in-plane tip-to-sensor distance in the image plane between the passive sensor and the tip of the intervention device based on the approximate angular orientation of the intervention device with respect to the image plane, and the fixed distance from the passive sensor to the tip of the intervention device.

In some embodiments, ascertaining the approximate angular orientation of the intervention device with respect to the image plane comprises using a history of previous positions of the intervention device and prediction of a future path of the intervention device by employing a Kalman model.

In some embodiments, ascertaining the approximate angular orientation of the intervention device with respect to the image plane comprises monitoring an insertion point of the intervention device within a patient to estimate a trajectory of the needle.

In some embodiments, ascertaining the approximate angular orientation of the intervention device with respect to the image plane comprises segmenting a shaft of the intervention device in the acoustic images.

In some embodiments, ascertaining the approximate angular orientation of the intervention device with respect to the image plane comprises finding a best fit match to: a history of previous positions of the intervention device and prediction of a future path of the intervention device by employing a Kalman model; a monitored insertion point of the intervention device within a patient; and a segmented shaft of the intervention device in the acoustic images.

In yet another aspect of the invention, an acoustic imaging instrument comprises: a receiver interface configured to receive a sensor signal from a passive sensor disposed on a surface of an intervention device which is disposed in an area of interest, wherein the passive sensor is located at a fixed distance from the tip of the intervention device; and a processor configured to ascertain an estimated range of locations of the tip of the intervention device in an image plane which is imaged by the acoustic imaging instrument. The processor is configured to ascertain the estimated range of locations of the tip of the intervention device in the image plane from the sensor signal and an estimated effective distance, projected onto the image plane, from the passive sensor to the tip of the intervention device.

In some embodiments, the instrument further comprises a display device configured to display the acoustic images of the image plane in the area of interest and one or more markers to indicate on the acoustic images the estimated range of locations of the tip of the intervention device in the image plane.

In some embodiments, the one or more markers includes a circle having a first color for a majority of its circumference and having a second color for an arc of less than 90 degrees, wherein the second color indicates most likely locations of the tip of the intervention device.

In some embodiments, the one or more markers includes a first circle having a circumference defining the estimated range of locations of the tip of the intervention device in the image plane, wherein the display device is further configured to display a second circle having a diameter equal to the fixed distance from the passive sensor to the tip of the intervention device.

BRIEF DESCRIPTION OF THE DRAWINGS

FIG. 9 illustrates a flowchart of an example embodiment of a method of improving estimates of the location of a tip of an intervention device in acoustic images.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. Herein, when something is said to be "approximately" or "about" a certain value, it means within 10% of that value.

In order to illustrate the principles of the present invention, various systems are described in which the position of the tip of an intervention device, exemplified by a surgical needle, is determined within the image plane of an acoustic field defined by the beams emitted by a 2D acoustic imaging probe. It is however to be appreciated that the invention also finds application in determining the positon of other intervention devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device.

It is also to be appreciated that the invention nay find application in beamforming acoustic imaging systems having other types of imaging probes and other types of acoustic arrays which are arranged to provide a planar image, such as the linear array of a 2D acoustic imaging probe, a transrectal ultrasonography probe, an intravascular acoustic probe, a transesophageal probe, a transthoracic probe, a transnasal probe, an intracardiac probe, etc.

Figure 1:
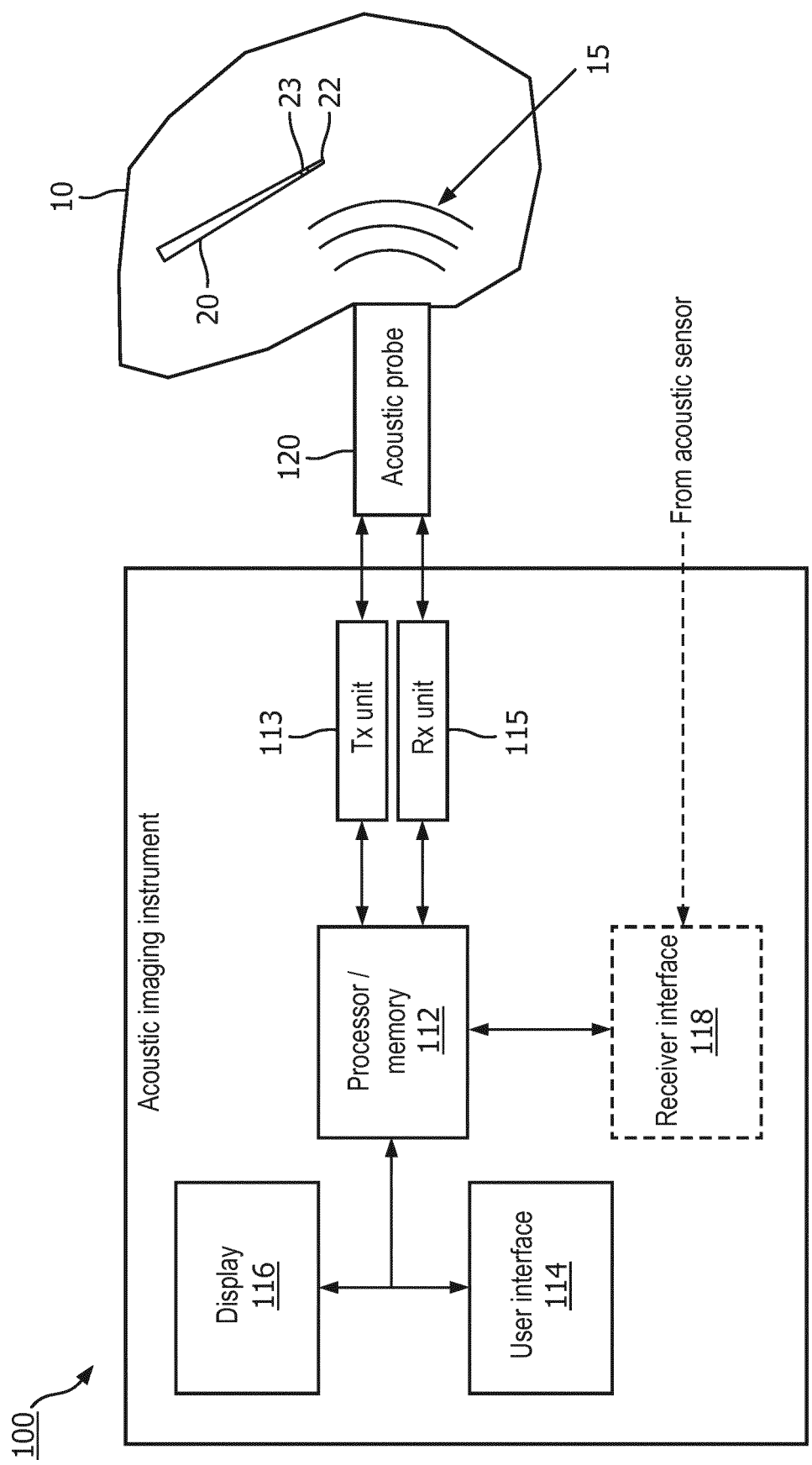
FIG. 1 shows one example of an acoustic imaging system, including an acoustic imaging instrument and an acoustic probe.

FIG. 1 shows one example of an acoustic imaging system 100 which includes an acoustic imaging instrument 110 and an acoustic probe 120. Acoustic imaging instrument 110 include a processor (and associated memory) 112, a transmit unit 113, a user interface 114, a receive unit 115, a display device 116 and a receiver interface 118, connected as shown in FIG. 1.

In various embodiments, processor 112 may include various combinations of a microprocessor (and associated memory), a digital signal processor, an application specific integrated circuit (ASIC), a field programmable gate array (FPGA), digital circuits and/or analog circuits. Memory (e.g., nonvolatile memory) associated with processor 112 may store therein computer-readable instructions which cause a microprocessor of processor 112 to execute an algorithm to control acoustic imaging system 100 to perform one or more operations or methods which are described in greater detail below. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", nonvolatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In some embodiments, a microprocessor may execute an operating system. In some embodiments, a microprocessor may execute instructions which present a user of acoustic imaging system 100 with a graphical user interface (GYI) via user interface 114 and display device 116.

In various embodiments, user interface 114 may include any combination of a keyboard, keypad, mouse, trackball, stylus/touch pen, joystick, microphone, speaker, touchscreen, one or more switches, one or more knobs, one or more buttons, one or more lights, etc. In some embodiments, a microprocessor of processor 112 may execute a software algorithm which provides voice recognition of a user's commands via a microphone of user interface 114.

Display device 116 may comprise a display screen of any convenient technology (e.g., liquid crystal display). In some embodiments the display screen may be a touchscreen device, also forming part of user interface 114.

Transmit unit 113 may generate one or more electrical transmit signals under control of processor 112 and supply the electrical transmit signals to acoustic probe 120. Transmit unit 113 may include various circuits as are known in the art, such as a clock generator circuit, a delay circuit and a pulse generator circuit, for example. The clock generator circuit may be a circuit for generating a clock signal for setting the transmission timing and the transmission frequency of a drive signal. The delay circuit may be a circuit for setting delay times in transmission timings of drive signals for individual paths corresponding to the transducer elements of acoustic probe 120 and may delay the transmission of the drive signals for the set delay times to concentrate the acoustic beams to produce acoustic probe signal 15 having a desired profile for insonifying a desired image plane. The pulse generator circuit may be a circuit for generating a pulse signal as a drive signal in a predetermined cycle.

Beneficially, acoustic probe 120 may include an array of acoustic transducer elements 122 (see FIG. 3), for example a 2D array. For example, in some embodiments, transducer elements 122 may comprise piezoelectric elements. In operation, at least some of acoustic transducer elements 122 receive electrical transmit signals from transmit unit 113 of acoustic imaging instrument 110 and convert the electrical transmit signals to acoustic beams to cause the array of acoustic transducer elements 122 to transmit an acoustic probe signal 15 to an area of interest 10. Acoustic probe 120 may insonify an image plane in area of interest 10 and a relatively small region on either side of the image plane (i.e., it expands to a shallow field of view).

Also, at least some of acoustic transducer elements 122 of acoustic probe 120 receive acoustic echoes from area of interest 10 in response to acoustic probe signal 15 and convert the acoustic echoes to electrical receive signals which are communicated to receive unit 115.

Receive unit 115 is configured to receive the electrical receive signals from transducer elements 122 of acoustic probe 120 and to process the electrical receive signals to produce to produce acoustic data. Receive unit 115 may include various circuits as are known in the art, such as one or more amplifiers, one or more A/D conversion circuits, and a phasing addition circuit, for example. The amplifiers may be circuits for amplifying the electrical receive signals at amplification factors for the individual paths corresponding to the transducer elements 122. The A/D conversion circuits may be circuits for performing analog/digital conversion (A/D conversion) on the amplified electrical receive signals. The phasing addition circuit is a circuit for adjusting time phases of the amplified electrical receive signals to which A/D conversion is performed by applying the delay times to the individual paths respectively corresponding to the transducer elements 122 and generating acoustic data by adding the adjusted received signals (phase addition).

Processor 112 may reconstruct acoustic data received from receiver unit 115 into an acoustic image corresponding to the image plane which intercepts area of interest 10, and subsequently causes display device 116 to display this image. The reconstructed image may for example be an ultrasound Brightness-mode "B-mode" image, otherwise known as a "2D mode" image, a "C-mode" image or a Doppler mode image, or indeed any ultrasound planar image.

Acoustic imaging instrument 110 may also include receiver interface 118 which is configured to receive one or more electrical signals (sensor signals) from an external passive acoustic sensor, for example an acoustic receiver disposed near a distal end (tip) 22 of an intervention device, as will be described in greater detail below, particularly with respect to FIG. 2.

Of course it is understood that acoustic imaging instrument 110 may include a number of other elements not shown in FIG. 1, for example a power system for receiving power from AC Mains, an input/output port for communications between processor 112 and acoustic probe 120, a communication subsystem for communicating with other eternal devices and systems (e.g., via a wireless, Ethernet and/or Internet connection), etc.

Figure 2:
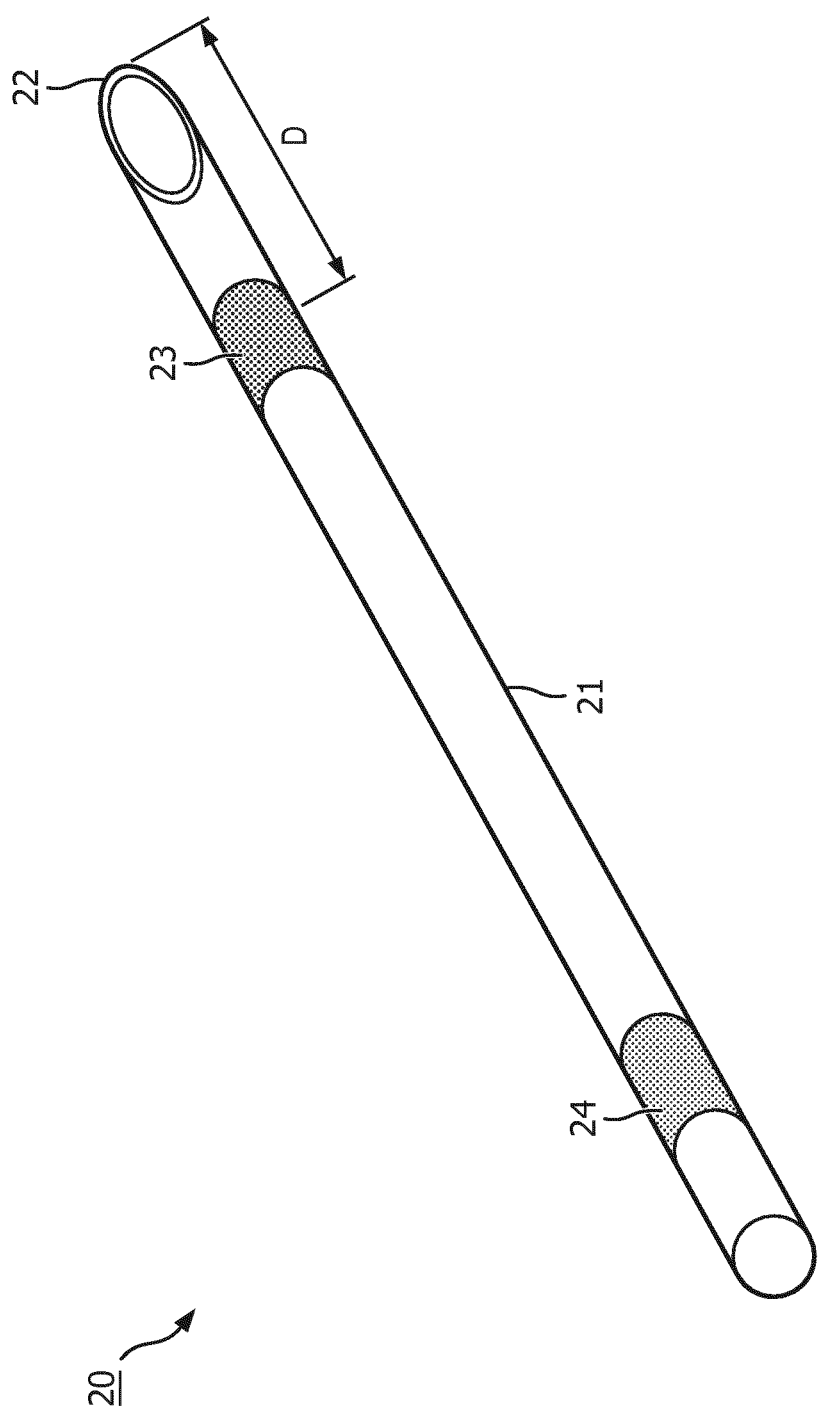
FIG. 2 illustrates one example embodiment of an intervention device having a sensor disposed at a distance from a top at a distal end thereof.

FIG. 2 illustrates one example embodiment of an intervention device 20 having an acoustic sensor (e.g., a passive acoustic sensor) 23 disposed near a distal end or tip 22 thereof. Acoustic sensor 23 is adapted for detecting ultrasound signals emitted by an ultrasound transducer array of a beamforming acoustic imaging system, such as acoustic imaging system 100 of FIG. 1. Acoustic sensor 23 is provided on a surface of shaft 21 of intervention device 20 at a predetermined distance D from tip 22 of intervention device 20.

Optionally, intervention device 20 also may include a data carrier 24 disposed on shaft 21 of intervention device 20. Data carrier 24 may include data indicative of a type T of intervention device 20. Moreover, this data, when received by processor 112 of acoustic imaging instrument 110, causes processor 112 to: i) ascertain a distance D between acoustic sensor 23 and tip 22 of intervention device 20 for the intervention device type T; and to ii) use the knowledge of the distance D to indicate in the reconstructed ultrasound image the estimated location(s) of tip 22 of intervention device 20 within the acoustic image.

In FIG. 2, data carrier 24 may for example be a barcode such as a linear or matrix barcode or a QR code, an RFID chip, a memory, or indeed any machine-readable data carrier. The data carrier may be attached to the intervention device by various known means including adhesives, or it may be applied by printing, etching, and the like. Also, whilst illustrated as being disposed on intervention device 20, data carrier 24 may alternatively be positioned on the packaging of intervention device 20, for example for sterility reasons. Thus, when the intervention device 20 is used with acoustic imaging system 100, the data received by processor 112 enables the technical effect of improved determination of the position of tip 22 of intervention device 20 respective the image plane of acoustic imaging system 100.

In some embodiments, data carrier 24 may be omitted. In that case, the distance D between acoustic sensor 23 and tip 22 of intervention device 20 may be communication to processor 112 of acoustic imaging system 100 by other techniques. For example, in some embodiments a clinician or user of acoustic imaging system 100 may enter the distance D directly via user interface 114. In other embodiments, memory (e.g., nonvolatile memory) associated with processor 112 may store a look up table containing entries for a plurality of different types of models of intervention device 20, where each entry includes a device type or model number and a corresponding distance D. In that case, the clinician or user of acoustic imaging system 100 may enter the type or model number via user interface 114 and processor 112 may ascertain the corresponding distance D from the look-up table. In still other embodiments where acoustic imaging instrument 110 includes a communication port for accessing a remote computer network, such as the Internet, processor 112 may access a remote database to ascertain the distance D between acoustic sensor 23 and tip 22 of intervention device 20. Other arrangements are contemplated.

Beneficially acoustic sensor 23 illustrated in FIGS. 1 and 2 may be a passive sensor and may be provided by a number of piezoelectric materials, both hard and soft piezoelectric materials being suitable. In some embodiments, acoustic sensor 23 may comprise polyvinylidene fluoride, otherwise known as PVDF whose mechanical properties and manufacturing processes lend themselves to attachment to curved surfaces such as needles. Alternative materials include a PVDF copolymer such as polyvinylidene fluoride trifluoroethylene, a PVDF ter-polymer such as 5 P(VDF-TrFE-CTFE). Acoustic sensor 23 may include various wires or a wireless communication module that are not shown in FIG. 2 for communicating a sensor signal generated in response to detected acoustic signals with receiver interface 118. Beneficially there may be a single, i.e. one and only one, such acoustic sensor 23 disposed on intervention device 20. Advantageously this simplifies the form factor of intervention device 20, any electrical interconnect that may be present, and the processing of any detected acoustic signals.

As described in greater detail below, in some embodiments processor 112 of acoustic imaging instrument 110 may use one or more sensor signals received by receiver interface 118 from passive acoustic sensor 23 disposed on intervention device 20 to track the location of intervention device 20, and particularly tip 22 thereof, in acoustic images generated from acoustic data produced by echoes received by acoustic probe 120.

In various embodiments, intervention device 20 may comprise a needle, a catheter, a guidewire, a probe, an endoscope, an intravenous line, a drainage line, a surgical tool such as a tissue sealing device or a tissue cutting device, etc.

Figure 3:
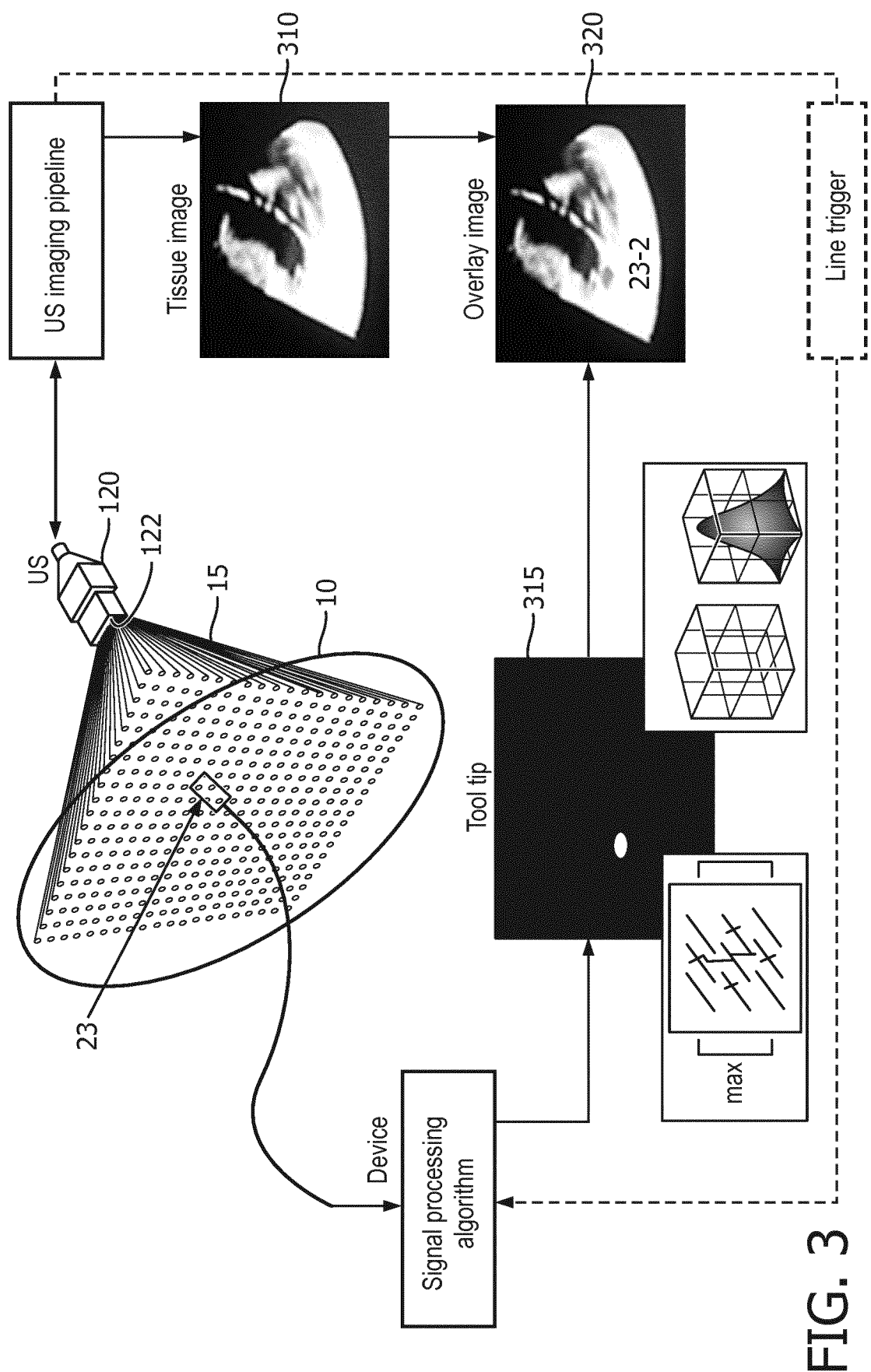
FIG. 3 illustrates example embodiment of a process of overlaying imaging produced from a sensor signal received from an acoustic sensor with an acoustic image produced from an acoustic probe.

FIG. 3 illustrates example embodiment of a process of overlaying imaging produced from one or more sensor signals received from a sensor, such as passive acoustic sensor 23, with an acoustic image produced from acoustic echoes received by an acoustic probe such as acoustic probe 120.

As illustrated in FIG. 3, acoustic probe 120 illuminates area of interest 10 with acoustic probe signal 15 and receives acoustic echoes from area of interest 10 in response to acoustic probe signal 15. An acoustic imaging instrument (e.g., acoustic imaging instrument 110) produces acoustic images 310 of area of interest 10 in response to acoustic echoes received from area of interest 10 in response to acoustic probe signal 15. In particular, acoustic probe 120 may communicate one or more electrical receive signals (electrical signals) to acoustic imaging instrument 110 in response to acoustic echoes received from area of interest 10 in response to acoustic probe signal 15, and acoustic imaging instrument 110 may produce acoustic images 310 from the electrical receive signal(s).

Meanwhile, a receiver interface (e.g., receiver interface 118) receives one or more electrical sensor signals from a passive acoustic sensor (e.g., passive acoustic sensor 23) disposed on a surface of an intervention device (e.g., device 20) disposed in area of interest 10, the one or more sensor signals being produced in response to acoustic probe signal 15.

A processor (e.g., processor 112) executes an algorithm to ascertain or determine, from the one or more sensor signals from passive acoustic sensor 23 an estimated range of locations of acoustic sensor 210 in area of interest 10. Image 315 illustrates sensor data obtained by processor 112, showing a marker 23-2 which identifies an estimated range of locations of passive acoustic sensor 23. For example, processor 112 may employ an algorithm to detect a maximum value or intensity peak in sensor data produced from the one or more sensor signals from passive acoustic sensor 23, and may determine or ascertain an estimated range of locations of passive acoustic sensor 23 corresponding to the location of an intensity peak in the sensor data. Here it should be understood that, in general, tracking of passive acoustic sensor 23 may not be precisely accurate due to noise and other factors, and so marker 23-2 may accommodate a predetermined tracking error or uncertainty, which in some embodiments may typically be in a range of 0.5-1.0 mm by showing an estimated range of locations of passive acoustic sensor 23 as a circular marker with a center at the most likely location and the radius corresponding to the expected uncertainty (e.g., 0.5-1.0 mm). Then acoustic imaging instrument 110 may overlay the sensor data illustrated in image 315 with acoustic image 310 to produce an overlaid acoustic image 320 which includes marker 23-2 to indicate the an estimated range of locations of passive acoustic sensor 23.

The process described above with respect to FIG. 3 allows a display of a marker indicating an estimated range of locations of a sensor (e.g., passive acoustic sensor 23) in an acoustic image.

However, as explained above, in ultrasound-guided medical procedures the physician wants to be able to visually locate the current position of the needle tip (or catheter tip) 22 in acoustic images which are displayed on a display screen or monitor.

Described below are systems and methods of utilizing a known location in an acoustic image of a passive sensor which is disposed at a known distance from the tip of an intervention device to provide improved estimates for the location of the tip of the intervention device in the acoustic image.

In particular, for in-plane or near in-plane imaging, acoustic imaging system 100, and in particular processor 112 may be configured to ascertain an approximate angular orientation of the intervention device (e.g., intervention device 20) with respect to the image plane of the acoustic image, and may use this information to provide an improves estimate of the location of tip 22 in the acoustic image.

Figure 4:
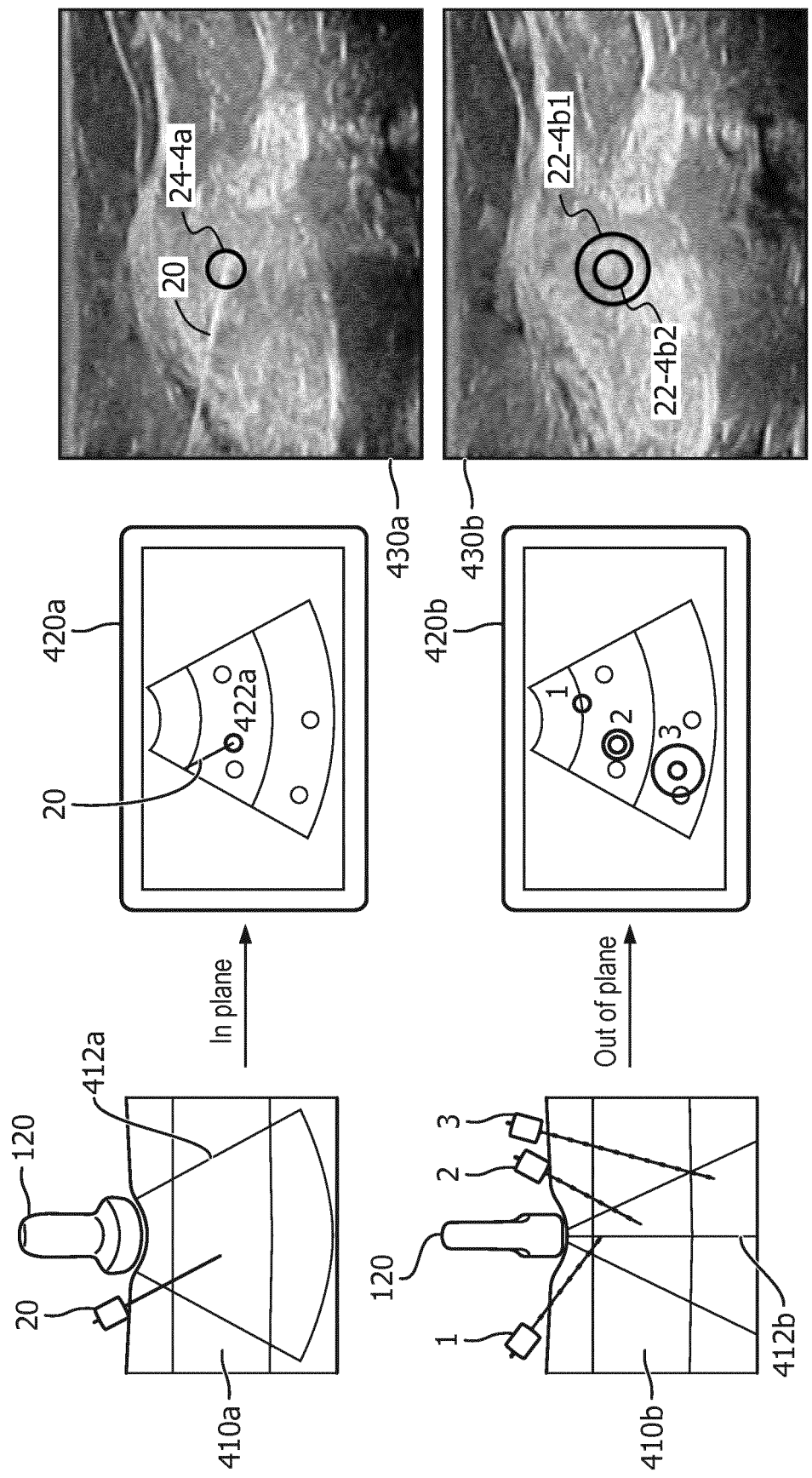
FIG. 4 illustrates of in-plane and out-of-plane imaging using an acoustic imaging instrument and an acoustic probe and a sensor signal received from an acoustic sensor.

FIG. 4 illustrates of in-plane and out-of-plane imaging using an acoustic imaging instrument and an acoustic probe and a sensor signal received from an acoustic sensor.

In particular, FIG. 4 shows at the top three illustrations for explaining in-plane imaging, and shows below that, at the bottom, three corresponding illustrations for explaining out-plane imaging.

Beginning at the top, FIG. 4 shows an illustration 410a which shows acoustic probe 120 insonifying an image plane 412a, where intervention device (needle) 20 is disposed in or at a slight angle with respect to image plane 412a, as an example of in-plane imaging. To the right of illustration 410a is shown an illustration 420a of a tip tracking display for tracking the location of tip 22 in image plane 412a for the case of in-plane imaging. Here the tip tracking display includes a marker 422a indicating an estimated range of locations of tip 22 of needle 20 in the image plane. Finally, to the right of illustration 420a is an illustration of an acoustic image 430a of the anatomical features of image plane 412a and needle 20 for the case of in-plane imaging. Superimposed on acoustic image 430a is a marker 24-4a indicating an estimated range of locations of tip 22 of needle 20.

Proceeding below, FIG. 4 also shows an illustration 410b which shows acoustic probe 120 insonifying an image plane 412a where three intervention devices, labeled 1, 2 and 3, are disposed perpendicular out of an image plane 412b, as an example of out-of-plane imaging. To the right of illustration 410b is shown an illustration 420b of a tip tracking display for tracking the locations of the tips of intervention devices 1, 2 and 3 in the image plane for the case of out-of-plane imaging. Here the tip tracking display includes markers indicating estimated ranges of locations for the tip of each of intervention devices 1, 2 and 3 in the image plane. For intervention device 1, whose tip is in or very near image plane 412b, the marker indicates a relatively small estimated range of locations for the tip, essentially corresponding to the distance D from the acoustic sensor (e.g., acoustic sensor 23) and the top (e.g. tip 22). For intervention devices 2 and 3, whose tips are relatively further from image plane 412b, two markers are shown: a smaller one indicating what the an estimated range of locations for the tip would be if the tip was in imaging plane 412b; and a larger one which factors in the additional uncertainty in the tip location due to the distance of the tip from image plane 412b. Finally, to the right of illustration 420b is an illustration of an acoustic image 430a of the anatomical features of image plane 412a and intervention device 2 for the case of out-of-plane imaging. Superimposed on acoustic image 430a are markers 22-4b1 and 22-4b2 indicating the estimated range of locations of tip 22 of needle 20 as described above.

The inventors have appreciated that an improvement in the estimated range of locations of the tip of an intervention device in an acoustic image for the case of in-plane imaging may be obtained by estimating the orientation angle of the intervention device with respect to the image plane and using the estimated orientation angle to determine an effective distance from the passive sensor to the tip in the image plane, where this effective distance may be less than the actual physical distance between the passive sensor and the tip. An explanation will now be provided with respect to FIGS. 5-9.

Figure 5:
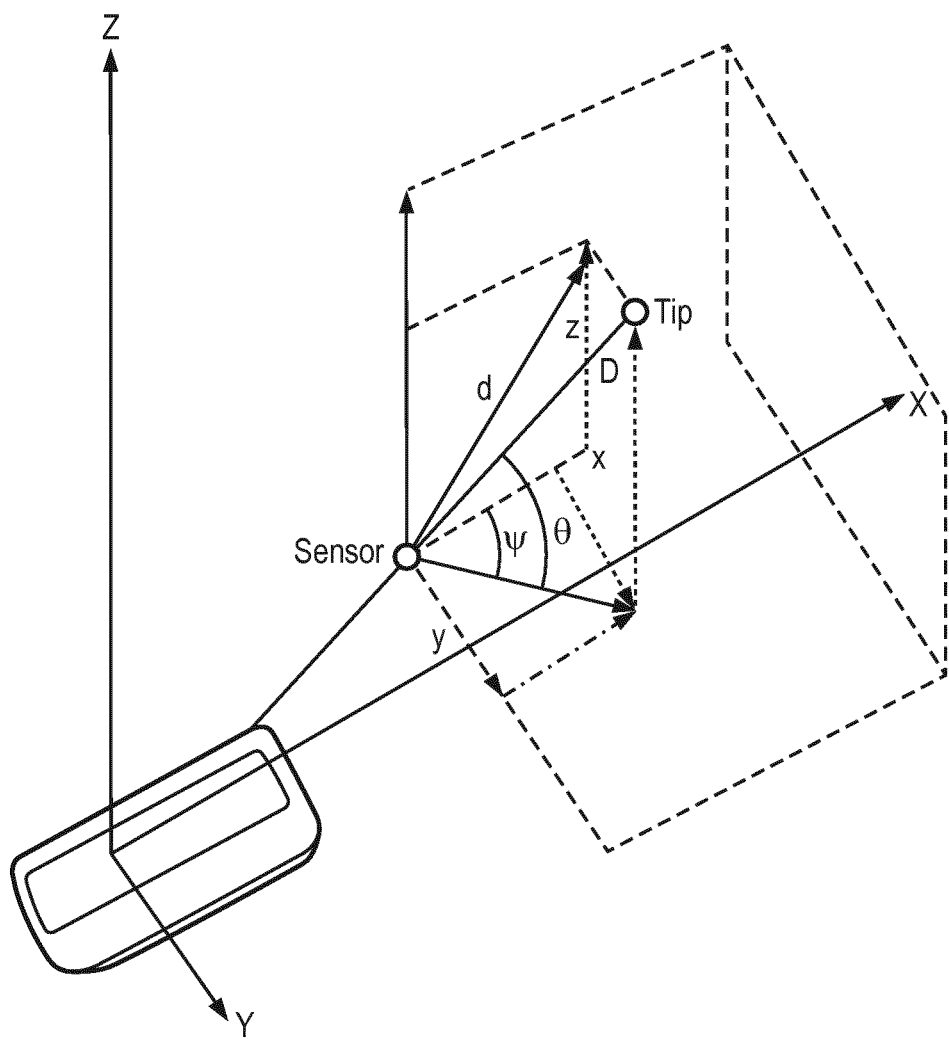
FIG. 5 illustrates the relationships between an image plane, the tip of an intervention device, and a sensor disposed on the surface of the intervention device at a distance D from the tip.

FIG. 5 illustrates the relationships between an image plane, the tip of an intervention device, and a sensor disposed on the surface of the intervention device at a distance D from the tip. Here the image plane is shown as the XZ plane. θ is the angle between the shaft of intervention device (e.g., needle) 20 and a projection in the XY plane. ψ is the angle between the projection in the XY plane and the X axis. D is the actual physical distance between acoustic sensor 23 and tip 22 of intervention device 20 and d is the effective distance in the image plane (XZ plane) between acoustic sensor 23 and tip 22 of intervention device 20. Furthermore, x, y, and z shown in FIG. 4 are found to be:

$$x = D*(\cos \psi)*(\cos \theta) \quad (1)$$

$$y = D*(\cos \theta)*(\cos \psi) \quad (2)$$

$$x = D*(\sin \theta) \quad (3)$$

In that case, it can be shown that:

$$d = \sqrt{x^2 + z^2} \quad (4)$$

$$d = D\sqrt{\sin^2\theta + \cos^2\theta \cos^2\varphi} \quad (5)$$

For the case where intervention device 20 is purely in-plane with respect to the image plane, then: ψ=0, x=0; y=0; z=D*sin θ; and the effective acoustic sensor-to-tip distance d=D.

For the case where intervention device 20 is purely out-of-plane with respect to the image plane, then: ψ=90°, x=0; y=D*cos θ; z=D*sin θ; and the effective acoustic sensor-to-tip distance d=D*sin θ<D.

It can further be shown that for an "average" out-of-plane condition where ψ=45° and θ=45°, then d≈0.886 D. Furthermore, for a nearly average out-of-plane case where ψ=45° and θ=60°, then d≈0.93 D.

Figure 6:
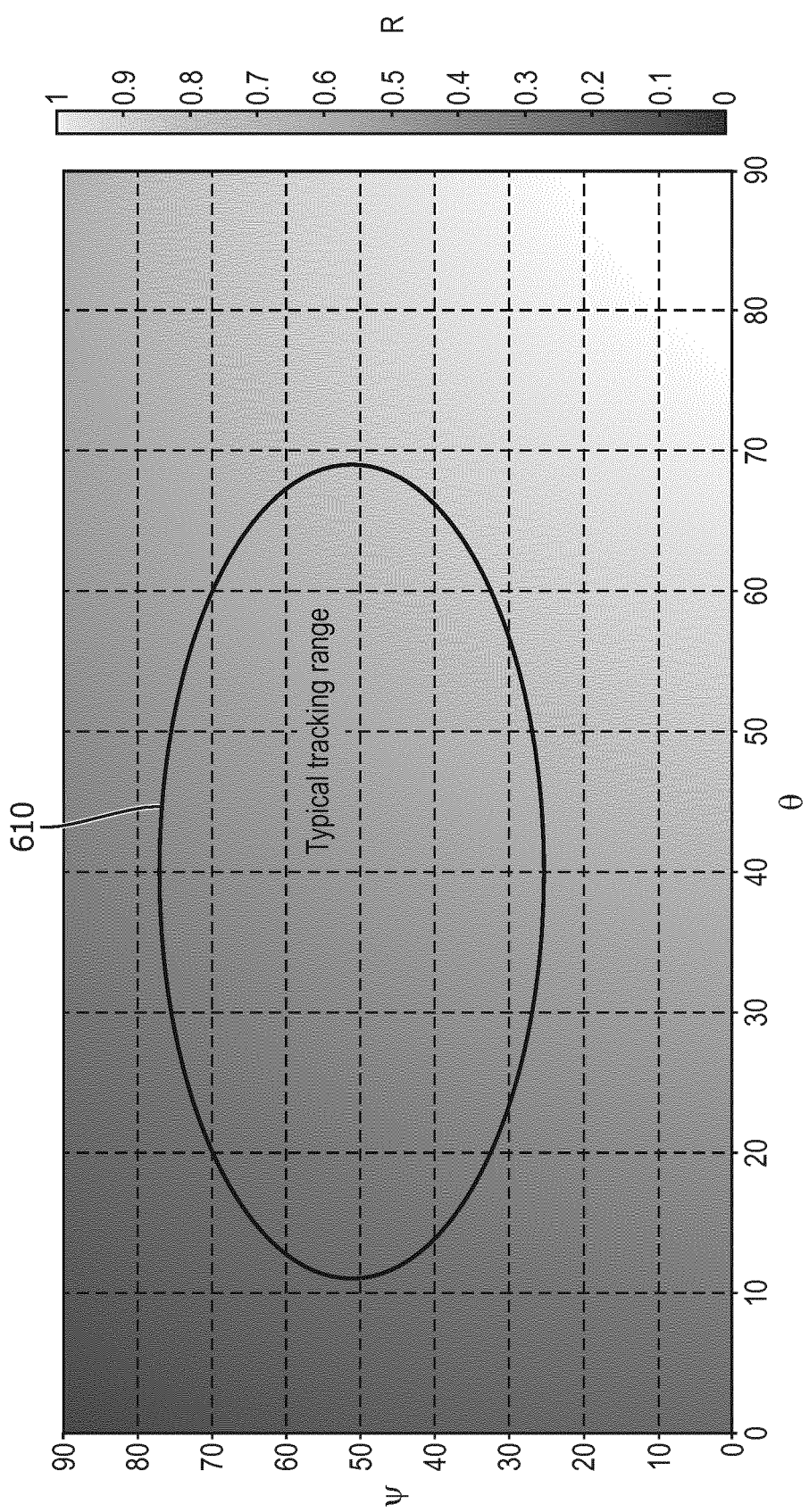
FIG. 6 illustrates a ratio R between an effective tip-sensor distance in an image plane and an actual tip-sensor distance, as a function of angles involving the image plane and a line extending from the sensor to the tip.

FIG. 6 illustrates a ratio R between an effective acoustic sensor-to-tip distance d in an image plane and an actual acoustic sensor-to-tip distance D, as a function of angles involving the image plane and a line extending from the acoustic sensor 23 to the tip 22. In particular, FIG. 6 illustrates the effective acoustic sensor-to-tip distance d in an image plane as a ratio R of the actual acoustic sensor-to-tip distance D for all possible in-plane and out-of-plane angles used in the computation where ψ and θ are allowed to range independently between 0 and 90 degrees. In most procedures the ratio R varies between 0.5 and 0.9, which presents an ability to provide an improved estimated range of locations of tip 22 in the acoustic image based on the determined location of acoustic sensor and the known actual acoustic sensor-to-tip distance D.

The inventors have also appreciated that an improvement in the estimated range of locations of the tip of an intervention device in an acoustic image for the case of in-plane imaging may be obtained by estimating the orientation angle of the intervention device with respect to the image plane and using the estimated orientation angle to identify an arc of less than 360°, and beneficially less than 90°, on a circle around the acoustic sensor having a radius equal to the effective acoustic sensor-to-tip distance d as the estimated range of locations of tip 22.

Figure 7:
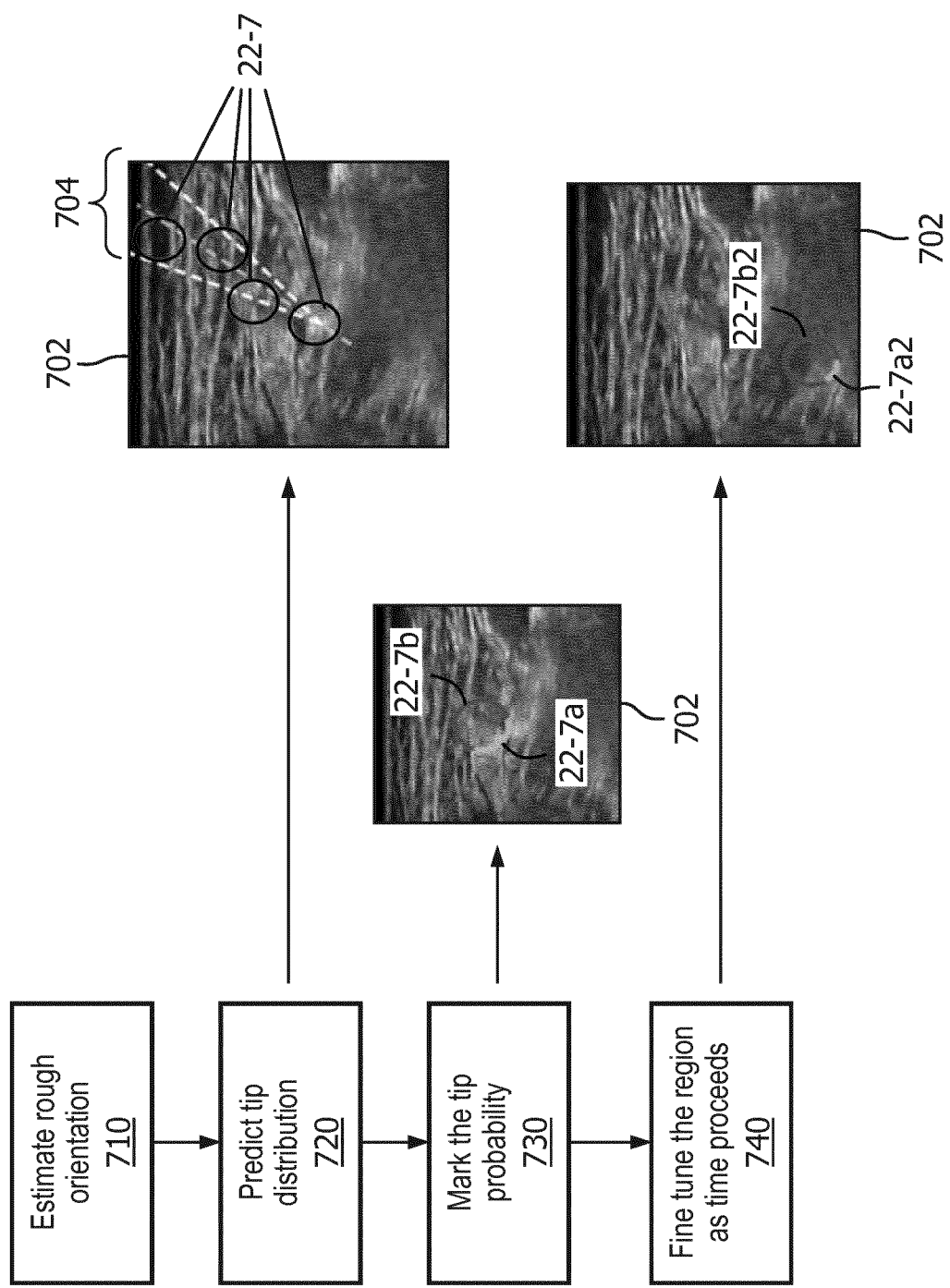
FIG. 7 illustrates one example embodiment of a method of improving an estimated location for the tip of an intervention device in acoustic images.

FIG. 7 illustrates one example embodiment of a method of improving an estimated location for the tip of an intervention device in acoustic images. The method illustrated in FIG. 7 may be performed by an acoustic imaging instrument (e.g., acoustic imaging instrument 110) under control of a processor (e.g., processor 112) executing instructions stored in memory.

Operation 710 estimates a rough orientation of intervention device (e.g., a needle) 20 with respect to the image plane (see image plane 412a in FIG. 4 above) for which an acoustic image is being generated. In particular, processor 112 of acoustic imaging instrument 110 may be configured, based on instructions stored in memory, to estimate the rough orientation of intervention device 20 with respect to the image plane In one embodiment, processor 112 is configured to ascertain the approximate angular orientation (e.g., ψ and θ—see FIG. 6 above) of intervention device 20 with respect to the image plane by using a history of previous positions of intervention device 20 and a prediction of a future path of intervention device 20 by employing a Kalman model.

In another embodiment, processor 112 is configured to ascertain the approximate angular orientation of intervention device 20 with respect to the image plane by monitoring an insertion point of intervention device 20 within a patient to estimate a trajectory of intervention device 20. This may include visually monitoring the insertion point to coarsely estimate the trajectory of intervention device 20 to estimate both in plane and out of plane orientation (see FIG. 6 above) and/or using a camera-based method to monitor the insertion point to estimate the in plane and out of plane orientation.

In still another embodiment, processor 112 is configured to ascertain the approximate angular orientation of intervention device 20 with respect to the image plane by segmenting shaft 21 of intervention device 20 in the acoustic images.

In yet another embodiment, processor 112 may be configured to ascertain the approximate angular orientation of intervention device 20 with respect to the image plane by employing a combination of two or more of the techniques described above, for example by finding a best fit match to: the history of previous positions of intervention device 20 and prediction of a future path of intervention device 20 by employing a Kalman model; a monitored insertion point of intervention device 20 within a patient; and a segmented shaft 21 of intervention device 20 in the acoustic images.

Operation 720 predicts a distribution of likely locations of tip 22 in the acoustic image. In particular, processor 112 may be configured to ascertain an estimated range of locations of tip 22 of intervention device 20 in the image plane using: the estimated location of passive sensor 23 obtained by acoustic imaging instrument 110 from the sensor signal as described above; the approximate angular orientation of intervention device 20 with respect to the image plane; and the known distance D from passive sensor 23 to tip 22 of intervention device 20, as described above with respect to FIG. 6.

FIG. 7 shows an acoustic image 702 with a coarse estimate 704 of the angular orientation of intervention device 20 with respect to the image plane, here for example based on a history of previous positions of tip intervention device 20, shown as markers 22-7.

In some embodiments, processor 112 of acoustic imaging instrument 110 may ascertain the approximate angular orientation of intervention device 20 to within 30° of the actual angular orientation using the techniques described above. This may allow a reduction in the region or locations where tip 22 may lie relative to sensor location 23.

Operation 730 places one or more markers on the acoustic image to indicate the estimated range of locations of tip 22.

Figure 8:
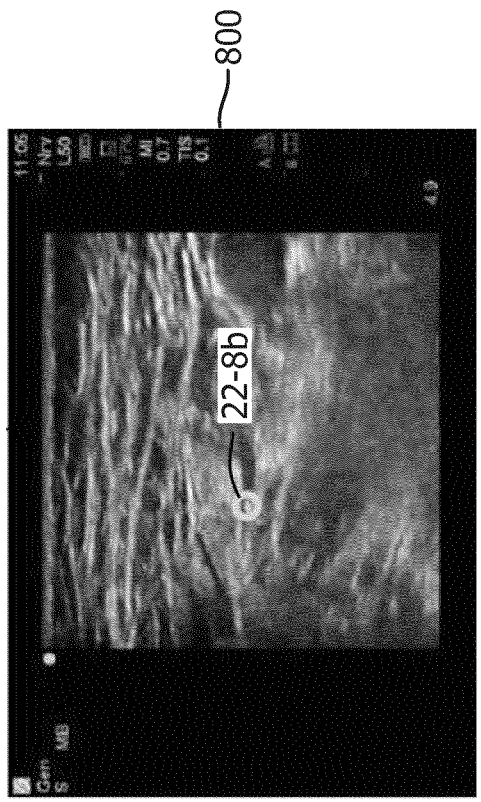
FIG. 8 illustrates various visualization options for showing the estimated locations of a tip of an intervention device in acoustic images.
Figure 8:
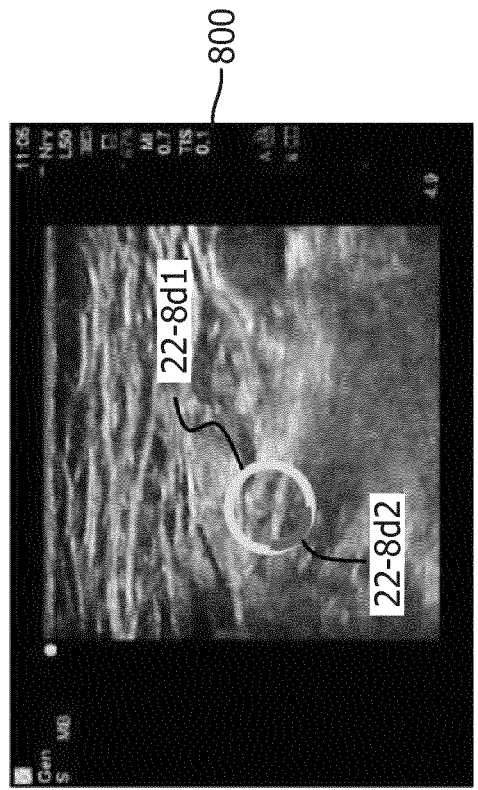
Figure 8:
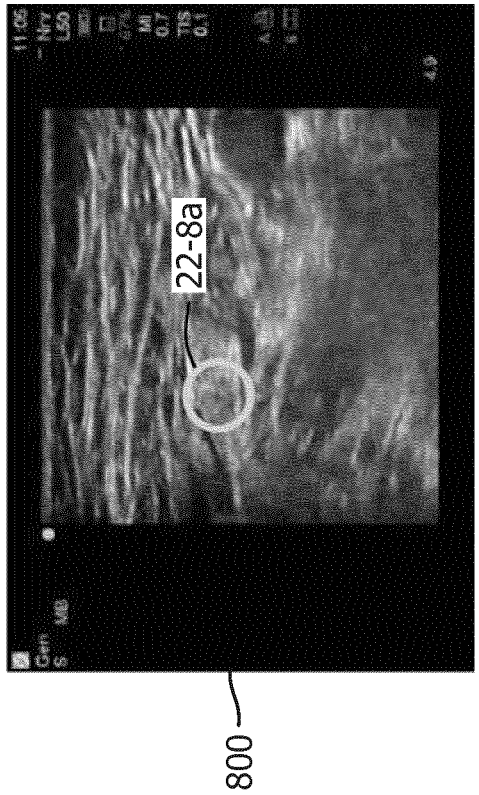
Figure 8:
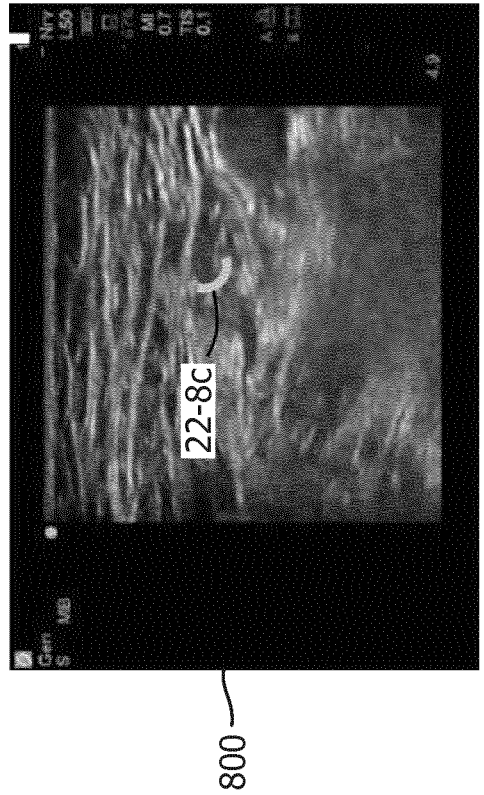

FIG. 8 illustrates various visualization options for showing the estimated locations of tip 22 of intervention device 20 in an acoustic image 800.

For example, without the improvements in the estimated locations of tip 22 of intervention device 20, acoustic imaging instrument 110 may display, via display device 116, a circular marker 22-8a designating a rather large region in the acoustic image for the estimated range of locations of tip 22.

In contrast, with the techniques described above the estimated range of locations of tip 22 may be reduced and accordingly acoustic imaging instrument 110 may display a circular marker 22-8a designating a considerably smaller region in the acoustic image for the estimated range of locations of tip 22.

In other embodiments, acoustic imaging instrument 110 may display an arc-shaped marker 22-8c designating a region in the acoustic image for the estimated range of locations of tip 22.

In still other embodiments, a combination of techniques may be employed. Acoustic imaging instrument 110 may display a circular marker 22-8d1 having a first color (e.g., green) designating a large region in the acoustic image for the estimated range of locations of tip 22 before the techniques above are applied, and an arc-shaped marker 22-8d2 having a second color (e.g., red) which designates a considerably smaller region in the acoustic image for the estimated range of locations of tip 22 by employing the techniques described above.

Here, FIG. 7 shows a circular marker 22-7b having a first color (e.g., red) designating a large region in the acoustic image for the estimated range of locations of tip 22 before the techniques above are applied, and an arc-shaped marker 22-7a having a second color (e.g., green) which designates a considerably smaller region in the acoustic image for the estimated range of locations of tip 22 by employing the techniques described above.

Operation 740 fine tunes the estimated range of locations of tip 22 as time progresses based on the history of previous estimates. FIG. 7 shows that at a later time acoustic imaging instrument 110 may display a circular marker 22-7b2 having the first color (e.g., red) designating a large region in the acoustic image for the estimated range of locations of tip 22 before the techniques above are applied, and an arc-shaped marker 22-7a2 having a second color (e.g., red) which designates a considerably smaller region in the acoustic image for the estimated range of locations of tip 22 by employing the techniques described above. Here it is seen that the size of arc-shaped marker 22-7a2 may be reduced over time, providing a clinician with an improving estimate for the location of tip 22 as time progresses.

FIG. 9 illustrates a flowchart of an example embodiment of a method of improving estimates of the location of a tip of an intervention device in acoustic images.

An operation 910 includes providing transmit signals to least some of the acoustic transducer elements of an acoustic probe (e.g., acoustic probe 120) to cause the array of acoustic transducer elements to transmit an acoustic probe signal to an area of interest (e.g., area of interest 10).

An operation 920 includes producing acoustic images of interest 10 in response to acoustic echoes received from area of interest 10 in response to the acoustic probe signal.

An operation 930 includes receiving one or more sensor signals from a sensor (e.g. sensor 23) disposed on a surface of an intervention device (e.g., intervention device 20) disposed in the area of interest, the one or more sensor signals being produced in response to the acoustic probe signal. Here, sensor 23 is located at a fixed distance D from tip 22 of intervention device 20.

An operation 940 includes identifying an estimated location of sensor 23 in the acoustic image, for example based on a localized intensity peak in sensor data.

An operation 950 includes ascertaining an approximate angular orientation of intervention device 20 with respect to the image plane, for example using techniques described above with respect to FIG. 7.

An operation 960 includes ascertaining an estimated range of locations of tip 22 of intervention device 20 in the image plane using the estimated location of sensor 23, the approximate angular orientation of intervention device 20 with respect to the image plane, and the known distance D from sensor 23 to tip 22 of intervention device 20.

An operation 970 includes displaying acoustic images on a display device (e.g., display 116)

An operation 980 includes displaying on display device 116 one or more markers to indicate on the acoustic images the estimated range of locations of tip 22 of intervention device 20 in the image plane.

It should be understood that the order of various operations in FIG. 9 may be changed or rearranged, and indeed some operations may actually be performed in parallel with one or more other operations. In that sense, FIG. 9 may be better viewed as a numbered list of operations rather than an ordered sequence.

While preferred embodiments are disclosed in detail herein, many variations are possible which remain within the concept and scope of the invention. Such variations would become clear to one of ordinary skill in the art after inspection of the specification, drawings and claims herein. The invention therefore is not to be restricted except within the scope of the appended claims.

The invention claimed is:

1. A system, comprising:
an acoustic probe having an array of acoustic transducer elements; and
an acoustic imaging instrument connected to the acoustic probe, the acoustic imaging instrument comprising:
a processor configured to:
provide transmit signals to at least one of the acoustic transducer elements to cause the array of acoustic transducer elements to transmit an acoustic probe signal to an area of interest,
produce acoustic images of an image plane of the area of interest in response to acoustic echoes received from the area of interest in response to the acoustic probe signal,
receive a sensor signal from a sensor disposed on a surface of an intervention device disposed in the area of interest, wherein the sensor signal is produced in response to the acoustic probe signal, and wherein the sensor is located at a fixed distance from a tip of the intervention device, estimate a location of the sensor from the sensor signal,
estimate an angular orientation of the intervention device with respect to the image plane, and
estimate a range of locations of the tip of the intervention device in the image plane based on the estimated location of the sensor, the estimated angular orientation of the intervention device with respect to the image plane, and the fixed distance from the sensor to the tip of the intervention device; and
a display device configured to display (i) the acoustic images of the image plane in the area of interest and (ii) one or more markers on the acoustic images to indicate the estimated range of locations of the tip of the intervention device in the image plane.

2. The system of claim 1, wherein the one or more markers includes a circle having a first color for a majority of its circumference and having a second color for an arc of less than 90 degrees, wherein the second color indicates most likely locations of the tip of the intervention device.

3. The system of claim 1, wherein the intervention device is a surgical needle.

4. The system of claim 1, wherein, to estimate the range of locations of the tip of the intervention device in the image plane, the processor is further configured to:
ascertain an in-plane tip-to-sensor distance between the sensor and the tip of the intervention device in the image plane based on the estimated angular orientation of the intervention device with respect to the image plane and the fixed distance from the sensor to the tip of the intervention device.

5. The system of claim 1, wherein, to estimate the angular orientation of the intervention device with respect to the image plane, the processor is further configured to use a history of previous positions of the intervention device and prediction of a future path of the intervention device by employing a Kalman model.

6. The system of claim 1, wherein, to estimate the angular orientation of the intervention device with respect to the image plane, the processor is further configured to:
monitor an insertion point of the intervention device within a patient to estimate a trajectory of the intervention device.

7. The system of claim 1, wherein, to estimate the angular orientation of the intervention device with respect to the image plane, the processor is further configured to:
segment a shaft of the intervention device in the acoustic images.

8. The system of claim 1, wherein, to estimate the angular orientation of the intervention device with respect to the image plane, the processor is further configured to;
find a best fit match to:
a history of previous positions of the intervention device and prediction of a future path of the intervention device by employing a Kalman model;
a insertion point of the intervention device monitored within a patient; and
a shaft of the intervention device segmented in the acoustic images.

9. The system of claim 1, wherein the processor is further configured to:
estimate a distance projected onto the image plane imaged from the sensor to the tip of the intervention device, and
estimated estimate the range of locations of the tip of the intervention device in the image plane based on the estimated distance projected onto the image plane.

10. The instrument of claim 9, further comprising a display device configured to display acoustic images of the image plane in the area of interest and one or more markers to indicate on the acoustic images the estimated range of locations of the tip of the intervention device in the image plane.

11. The instrument of claim 10, wherein the one or more markers comprises a circle having a first color for a majority of its circumference and having a second color for an arc of less than 90 degrees, wherein the second color indicates most likely locations of the tip of the intervention device.

12. The instrument of claim 10, wherein the one or more markers comprises a first circle having a circumference defining the estimated range of locations of the tip of the intervention device in the image plane, and wherein the display device is further configured to display a second circle having a diameter equal to the fixed distance from the sensor to the tip of the intervention device.

13. A method, comprising:
transmitting an acoustic probe signal to an area of interest;
producing acoustic images of an image plane of the area of interest in response to acoustic echoes received from the area of interest in response to the acoustic probe signal;
receiving a sensor signal from a sensor disposed on a surface of an intervention device in the area of interest, wherein the sensor signal is produced in response to the acoustic probe signal, and wherein the sensor is located at a fixed distance from a tip of the intervention device;
estimating a location of the sensor from the sensor signal;
estimating an angular orientation of the intervention device with respect to the image plane;
estimating a range of locations of the tip of the intervention device in the image plane using based on the estimated location of the sensor, the estimated angular orientation of the intervention device with respect to the image plane, and the fixed distance from the sensor to the tip of the intervention device;
displaying (i) the acoustic images and (ii) one or more markers on the acoustic images to indicate the estimated range of locations of the tip of the intervention device in the image plane.

14. The method of claim 13, wherein the one or more markers includes a circle having a first color for a majority of its circumference and having a second color for an arc of less than 90 degrees, wherein the second color indicates most likely locations of the tip of the intervention device.

15. The method of claim 13, wherein the intervention device is a surgical needle.

16. The method of claim 13, wherein estimating the range of locations of the tip of the intervention device in the image plane comprises ascertaining an in-plane tip-to-sensor distance in the image plane between the sensor and the tip of the intervention device based on the estimated angular orientation of the intervention device with respect to the image plane and the fixed distance from the sensor to the tip of the intervention device.

17. The method of claim 13, wherein estimating the angular orientation of the intervention device with respect to the image plane comprises using a history of previous positions of the intervention device and prediction of a future path of the intervention device by employing a Kalman model.

18. The method of claim 13, wherein estimating the angular orientation of the intervention device with respect to the image plane comprises monitoring an insertion point of the intervention device within a patient to estimate a trajectory of the intervention device.

19. The method of claim 13, wherein estimating the angular orientation of the intervention device with respect to the image plane comprises segmenting a shaft of the intervention device in the acoustic images.

20. The method of claim 13, wherein estimating the angular orientation of the intervention device with respect to the image plane comprises finding a best fit match to:
   a history of previous positions of the intervention device and prediction of a future path of the intervention device by employing a Kalman model;
   a insertion point of the intervention device monitored within a patient; and
   a shaft of the intervention device segmented in the acoustic images.

21. A non-transitory computer readable medium comprising instructions which, when executed by a processor, cause the processor to:
   provide transmit signals to at least one of the acoustic transducer elements to cause the array of acoustic transducer elements to transmit an acoustic probe signal to an area of interest;
   produce acoustic images of an image plane of the area of interest in response to acoustic echoes received from the area of interest in response to the acoustic probe signal;
   receive a sensor signal from a sensor disposed on a surface of an intervention device disposed in the area of interest, wherein the sensor signal is produced in response to the acoustic probe signal, and wherein the sensor is located at a fixed distance from a tip of the intervention device;
   estimate a location of the sensor from the sensor signal;
   estimate an angular orientation of the intervention device with respect to the image plane;
   estimate a range of locations of the tip of the intervention device in the image plane based on the estimated location of the sensor, the approximate angular orientation of the intervention device with respect to the image plane, and the fixed distance from the sensor to the tip of the intervention device; and
   display (i) the acoustic images of the image plane in the area of interest and (ii) one or more markers on the acoustic images to indicate the estimated range of locations of the tip of the intervention device in the image plane.

* * * * *